United States Patent
Xu et al.

(10) Patent No.: US 11,214,596 B2
(45) Date of Patent: Jan. 4, 2022

(54) METHOD FOR PRODUCING SURFACTIN BY USING BACILLUS AMYLOLIQUEFACIENS

(71) Applicant: Jiangnan University, Wuxi (CN)

(72) Inventors: Yan Xu, Wuxi (CN); Qun Wu, Wuxi (CN)

(73) Assignee: Jiangnan University, Wuxi (CN)

( * ) Notice: Subject to any disclaimer, the term of this patent is extended or adjusted under 35 U.S.C. 154(b) by 378 days.

(21) Appl. No.: 16/220,147

(22) Filed: Dec. 14, 2018

(65) Prior Publication Data

US 2019/0144505 A1     May 16, 2019

Related U.S. Application Data

(63) Continuation of application No. PCT/CN2017/082424, filed on Apr. 28, 2017.

(30) Foreign Application Priority Data

Sep. 26, 2016 (CN) .......................... 201610852329.X

(51) Int. Cl.
| | |
|---|---|
| C07K 7/64 | (2006.01) |
| C09K 8/582 | (2006.01) |
| A61K 35/74 | (2015.01) |
| C07K 7/06 | (2006.01) |
| C12N 1/20 | (2006.01) |
| C09K 8/584 | (2006.01) |
| C12P 21/02 | (2006.01) |
| A61K 38/12 | (2006.01) |
| C12R 1/07 | (2006.01) |

(52) U.S. Cl.
CPC ............... *C07K 7/64* (2013.01); *A61K 35/74* (2013.01); *A61K 38/12* (2013.01); *C07K 7/06* (2013.01); *C09K 8/582* (2013.01); *C09K 8/584* (2013.01); *C12N 1/20* (2013.01); *C12N 1/205* (2021.05); *C12P 21/02* (2013.01); *C12R 2001/07* (2021.05)

(58) Field of Classification Search
None
See application file for complete search history.

(56) References Cited

FOREIGN PATENT DOCUMENTS

| CN | 101418271 A | 4/2009 |
|---|---|---|
| CN | 103243044 A | 8/2013 |
| CN | 105695543 A | 6/2016 |

OTHER PUBLICATIONS

Zhi, Y. et al., "Genome and Transcriptome Analysis of Surfactin Biosynthesis in Bacillus Amyloliquefaciens MT45", Scientific Reports, vol. 7, Jan. 23, 2017(Jan. 23, 2017), article 40976.
Rong, Yanjun, "Antibacterial Activity of the Lipopeptides Produced by Bacillus amyloliquefaciens R3 against Multidrug-resistant Pathogenic *E. coli*", China Master's Theses Full-Text Database(Basic Sciences), Feb. 15, 2015 (Feb. 15, 2015), pp. A006-227.
Zhang Bao:"Purification, Identification and Mechanism of Action of Lipopeptide Antibiotic Bacillomycin L Produced by Bacillus amyloliquefaciens", Science-Engineering(A), China Doctoral Dissertations Full-Text Database, Aug. 15, 2014(Aug. 15, 2014), pp. B024-9.
Tang, Minxin et al., "Effect of Bacillus amyloliquefaciens ES-2 on Carcass Characteristics, Meat Quality and Antioxidative Status of Broilers", Journal of Nanjing Agricultural University, Mar. 30, 2016(Mar. 30, 2016) pp. 255-261.

*Primary Examiner* — Robert J Yamasaki
(74) *Attorney, Agent, or Firm* — IPRO, PLLC; Na Xu

(57) ABSTRACT

The invention discloses a method for producing surfactin by using *Bacillus amyloliquefaciens*, belonging to the technical field of industrial microorganisms. The invention synthesizes surfactin by using the screened *Bacillus amyloliquefaciens* CGMCC No. 12593, the yield is up to 9.43 g/L, and a fermentation process has the characteristics that the surfactin synthesis and the growth of the strain are synchronous without a lag period. The strain and the fermentation method provided by the invention will play an important role in the industrial production of surfactin and have broad application prospects.

6 Claims, 3 Drawing Sheets

Specification includes a Sequence Listing.

METHOD FOR PRODUCING SURFACTIN BY USING BACILLUS AMYLOLIQUEFACIENS

TECHNICAL FIELD

The disclosure herein relates to a method for producing surfactin by using *Bacillus amyloliquefaciens*, belonging to the technical field of industrial microorganisms.

BACKGROUND

Surfactin is a cyclic lipopeptide linked by a long-chain fatty acid ($C_{12}$-$C_{17}$) and a polypeptide containing seven amino acids via a lactone bond, which is synthesized by *Bacillus subtilis* through a nonribosomal peptide synthetase (NRPS) pathway. Surfactin has antibacterial, antiviral, antitumor, thrombolytic and cholesterol-lowering medicinal effects and a superior surface active function. The broad-spectrum antibacterial effect of surfactin is expected to make up for the ubiquitous antibiotic resistance problem nowadays. The antiviral and antitumor functions of surfactin also provide some options for the design of new drugs, while surfactin has broad application prospects in cosmetics, pharmaceuticals, emulsifiers, humectants and fine chemicals because of its superior surface active function (which can reduce the surface tension of water molecules from 72 mN/M to 27 mN/M). According to statistics, the output value of the world surfactant industry in 2006 was more than 20 billion U.S. dollars, of which North America, Western Europe and China accounted for more than 70% of market shares. As a superior biosurfactant, surfactin has shown broad application value and market prospects. Therefore, the development of microbial strains and production processes capable of efficiently synthesizing surfactin are of great significance for the industrial production and popularization of surfactin.

At present, the selection of producing bacteria of surfactin mainly adopts a method of combining mutation breeding and random screening. Although the surfactin yield of the mutagenized strain is improved, it still cannot be applied to industrial production due to low yield and poor stability of the strain. Screening a wild-type high-yield strain is still a primary task to achieve industrial production of surfactin.

According to literature reports, only some cells of *Bacillus* (*Bacillus subtilis*, *Bacillus amyloliquefaciens*) can synthesize surfactin during the growth of thalli, which in turn induces the formation of a biofilm. After a biofilm formation pathway of *Bacillus* is activated, the synthesis of surfactin is feedback-inhibited, and then the metabolic synthesis of surfactin is terminated. *Bacillus* in nature achieves the purpose of coping with environmental pressure and gaining competitive advantage by forming the biofilm, and thus has poor surfactin synthetic ability and can only synthesize the dose inducing biofilm formation. In addition, surfactin has antibiotic activity, and cytoplasmic leakage is formed via non-specifically attacking the phospholipid bilayer of a cell membrane, thereby achieving the purpose of killing microorganisms. This is another reason why most *Bacillus* cannot synthesize surfactin excessively. The original yield by wild-type *Bacillus* is generally 100-200 mg/L. Although the yield of surfactin can be increased to some extent after being subjected to a fermentation medium and fermentation condition, an expensive special fermentation equipment is required to continue to increase the yield of surfactin. For example, in the case of the application of a fermentation-membrane extraction coupling reactor, the highest yield of surfactin by *Bacillus subtilis* is about 6.5 g/L. Expensive production costs are the main reason why the surfactin still cannot be commercially produced. Therefore, the obtainment of a natural high-yield strain producing high level of surfactin, the improvement of production efficiency and the reduction of production cost are still fundamental solutions for the commercial application of surfactin.

SUMMARY

The invention first provides a *Bacillus amyloliquefaciens* MT45 strain synthesizing surfactin in a super-efficient way, which was deposited in China General Microbiological Culture Collection Center, Institute of Microbiology, Chinese Academy of Sciences, No. 3, Campus #1, Beichen West Road, Chaoyang District, Beijing, on Jun. 6, 2016 with the preservation number of CGMCC NO. 12593.

The colony morphology of the *Bacillus amyloliquefaciens* MT45 strain is that: colonies are round and translucent with smooth and not rugose surface, a biofilm is not formed, the central of colony is slightly convex, cells are rod-shaped under a microscope, spores are formed, and a Gram stain result is positive.

The invention also provides a method for producing surfactin by using the above *Bacillus amyloliquefaciens* MT45, including the following steps:

(1) picking a pure colony of *Bacillus amyloliquefaciens* CGMCC NO. 12593, and activating to obtain a seed culture solution;

(2) inoculating the seed culture solution obtained in the step (1) into a fermentation medium at an inoculum size of 1% to 5%, and culturing at 25 to 37° C. for 30 to 55 h.

In one embodiment of the invention, a formula of the seed medium is 2% of glucose, 1% of yeast powder, and 0.5% of sodium chloride, natural pH.

In one embodiment of the present invention, a formula of the fermentation medium is 10-100 g/L of carbon source, 1-10 g/L of nitrogen source, 0.1-1.5 g/L of peptone, 2-10 g/L of potassium dihydrogen phosphate, 2-10 g/L of disodium hydrogen phosphate, and 0-0.2 g/L of magnesium sulfate; the carbon source includes one or more of sucrose, glucose, fructose, mannose, chitosan, glycerol, soluble starch, and dextrin; the nitrogen source includes one or more of ammonium nitrate, ammonium sulfate, ammonium chloride, ammonium carbonate, and ammonium bicarbonate.

In one embodiment of the invention, the carbon source of the fermentation medium is sucrose, glucose, fructose, or glycerol.

In one embodiment of the invention, the carbon source of the fermentation medium is glucose or sucrose.

In one embodiment of the invention, the nitrogen source of the fermentation medium is ammonium nitrate, ammonium carbonate or ammonium sulfate.

In one embodiment of the present invention, the formula of the fermentation medium is 10-30 g/L of carbon source, 2-6 g/L of nitrogen source, 0.1-1.5 g/L of peptone, 2-10 g/L of potassium dihydrogen phosphate, 2-10 g/L of disodium hydrogen phosphate, and 0-0.2 g/L of magnesium sulfate.

In one embodiment of the present invention, the formula of the fermentation medium is 10-30 g/L of sucrose or glucose, 2-6 g/L of ammonium nitrate or sodium carbonate or ammonium sulfate, 0.1-1.5 g/L of peptone, 2-10 g/L of potassium dihydrogen phosphate, 2-10 g/L of disodium hydrogen phosphate, and 0.01-0.2 g/L of magnesium sulfate.

In one embodiment of the present invention, the formula of the fermentation medium is 30 g/L of sucrose, 6 g/L of ammonium nitrate, 0.5 g/L of peptone, 2-10 g/L of potassium dihydrogen phosphate, 2-10 g/L of disodium hydrogen phosphate, and 0.18 g/L of magnesium sulfate.

In one embodiment of the present invention, the formula of the fermentation medium is 10 g/L of sucrose, 6 g/L of ammonium nitrate, 1.5 g/L of peptone, 2 g/L of potassium dihydrogen phosphate, and 2 g/L of disodium hydrogen phosphate.

In one embodiment of the present invention, the formula of the fermentation medium is 30 g/L of sucrose, 6 g/L of ammonium nitrate, 0.5 g/L of peptone, 2-10 g/L of potassium dihydrogen phosphate, 2-10 g/L of disodium hydrogen phosphate, and 0.18 g/L of magnesium sulfate.

In one embodiment of the present invention, the formula of the fermentation medium is 10 g/L of sucrose, 6 g/L of nitrogen source, 1.5 g/L of peptone, 0.14 g/L of zinc sulfate, 4 g/L of potassium dihydrogen phosphate, 2 g/L of disodium hydrogen phosphate, and 0.18 g/L of magnesium sulfate.

In one embodiment of the present invention, in step (1), a pure colony of *Bacillus amyloliquefaciens* CGMCC NO. 12593 is picked and inoculated into a seed medium, which is cultured at a temperature of 37° C. and a shaker speed of 200 rpm for 24 h to obtain a seed culture solution.

The invention has the following beneficial effects.

The invention provides a novel *Bacillus amyloliquefaciens* MT45 strain, which is capable of synthesizing surfactin in a super-efficient way by using an inorganic salt medium. The strain synthesizes surfactin synchronizing with the growth of thalli, which has the characteristics that the product (surfactin) synthesis and the growth of the strain are synchronous without a lag period, the strain does not form a biofilm to avoid the feedback inhibition of the product and is highly tolerant to the product. The culture method provided by the invention can produce up to 9.43 g/L of surfactin via fermentation for 55 h by using preferred carbon and nitrogen sources and a preferred ratio of carbon source and nitrogen source, which can meet the requirements of industrial large-scale production and have great industrial application prospects.

Biomaterial Preservation:

*Bacillus amyloliquefaciens* was deposited in China General Microbiological Culture Collection Center, Institute of Microbiology, Chinese Academy of Sciences, No. 3, Campus #1, Beichen West Road, Chaoyang District, Beijing, on Jun. 6, 2016 with the preservation number of CGMCC NO. 12593.

DETAILED DESCRIPTION

Figure 1:
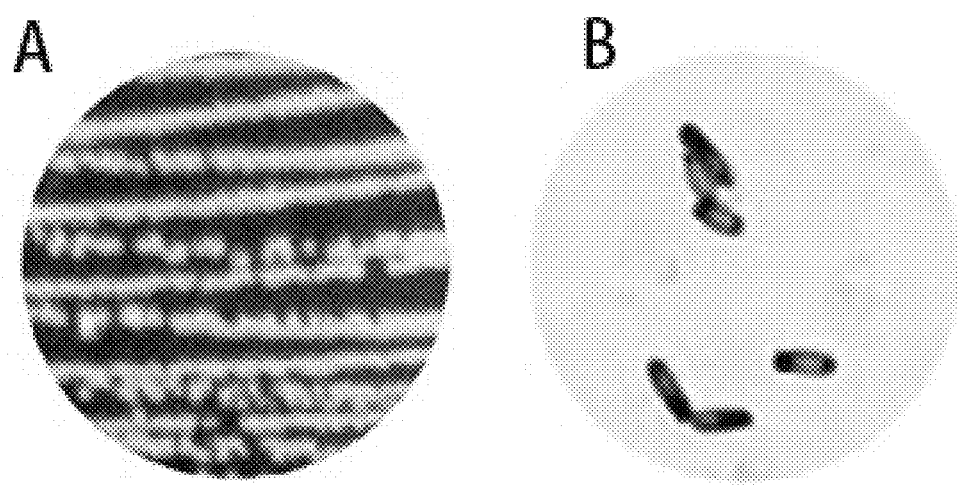
FIG. 1 shows the colony morphology (A) and micrograph (B) of *Bacillus amyloliquefaciens* MT45 on nutrient agar plates.

The composition of the activated culture solution is: based on mass percent, 1%-5% of glucose, 1%-5% of yeast powder, 0.3%-1.0% of sodium chloride, and the balance of water; pH 6.5-7.0.

The composition of the solid medium: 1-10 mM of potassium phosphate, 50-100 mM of Mops, 2-6 mM of magnesium chloride, 0.1-1 mM of calcium chloride, 10-80 µM of manganese chloride, 10-80 µM of ferric chloride, 2-6 µM of zinc chloride, 2-6 µM of thiamine, 0.1-1% of glycerol, 0.1-1% of glutamic acid, and 1%-2% of agar.

Nutrient medium: 2% of peptone, 1% of yeast powder, and 0.5% of glucose, pH 7.5.

Seed medium: 2% of glucose, 1% of yeast powder, and 0.5% of sodium chloride, natural pH.

Fermentation medium: 10-100 g/L of carbon source, 1-10 g/L of nitrogen source, 0.1-1.5 g/L of peptone, 2-10 g/L of potassium dihydrogen phosphate, 2-10 g/L of disodium hydrogen phosphate, and 0.01-0.1 g/L of magnesium sulfate.

Example 1 Screening of Strains

A sample were collected from high temperature Daqu (starter) of Chinese liquor fermentation, and a 5 g sample was dissolved in 10 ml of sodium chloride solution with the mass percent of 1%. After vortexing and mixing, 1 mL was pipetted and inoculated into the activated culture solution, which was activated at a temperature of 50-60° C. and at a speed of 200 rpm for 24-36 h to prepare a mature and activated bacterial solution.

The mature and activated bacterial solution was taken and diluted by adding a sodium chloride solution with the mass percent of 1%. A dilution with a dilution gradient of $10^{-2}$-$10^{-6}$ was selected and applied sequentially to a solid medium plate. The culture was carried out for 48-72 h at a temperature of 30° C. and a humidity of 40%-60%, and a large number of single colonies were obtained. After the obtained single colony was inoculated into the nutrient medium for fermentation and culture, the surfactin content in a fermentation broth was detected, and finally a pure culture producing high level of surfactin was obtained and numbered MT45.

Example 2 Method for Determining Surfactin

Extraction of surfactin: the fermentation broth was centrifuged at 8000 rpm, 4° C. for 10 min. A fermentation supernatant was adjusted to pH 2.0 with 6 mol/L of hydrochloric acid, allowed to stand in a refrigerator at 4° C. for 2 hours, and then centrifuged at 12,000 rpm, 4° C. for 30 min to obtain a precipitate. The precipitate was extracted with methanol to obtain crude surfactin.

Determination method of surfactin in fermentation broth: Accurate quantification of surfactin was carried out by ultra-performance liquid chromatography. The waters BEH C18 chromatographic column was used, and mobile phases were (A) 0.1% aqueous formic acid solution and (B) HPLC grade methanol, respectively. The elution condition is 30%-70% of methanol for 5 min and 70%-100% of methanol for 1 min. The sample was detected at 210 nm using a diode array detector. After integrating obtained chromatographic peaks, an interpolation method was used to compare with a standard curve to obtain the accurate content of surfactin.

Example 3 the Strain Identification of the Strain Screened in Example 1

The strain numbered MT45 and obtained in Example 1 was subjected to strain identification.

The *Bacillus amyloliquefaciens* MT45 strain formed round and translucent colonies on the solid plate medium. The surface of the colony was smooth and not rugose, and no biofilm represented by rugose colonies was formed. The central of colony was slightly convex. The cells were rod-shaped under the microscope, spores were formed, and a Gram stain result was positive (FIG. 1).

Figure 2:
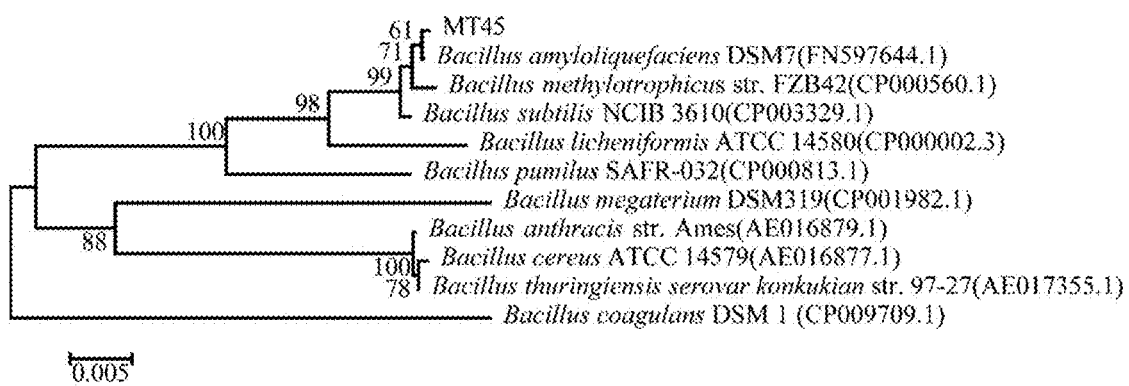
FIG. 2 is a phylogenetic tree of *Bacillus amyloliquefaciens* MT45 based on 16s rRNA sequence alignment.

The 16r rRNA gene sequence of the strain was sequenced (SEQ ID NO. 1) and compared with a database. A phylogenetic tree analysis was performed to identify MT45 as *Bacillus amyloliquefaciens* (FIG. 2).

*Bacillus amyloliquefaciens* MT45 was deposited in China General Microbiological Culture Collection Center on Jun. 6, 2016 with the preservation number of CGMCC NO. 12593.

Example 4 Fermentation Process of *Bacillus amyloliquefaciens* MT45

Figure 3A:
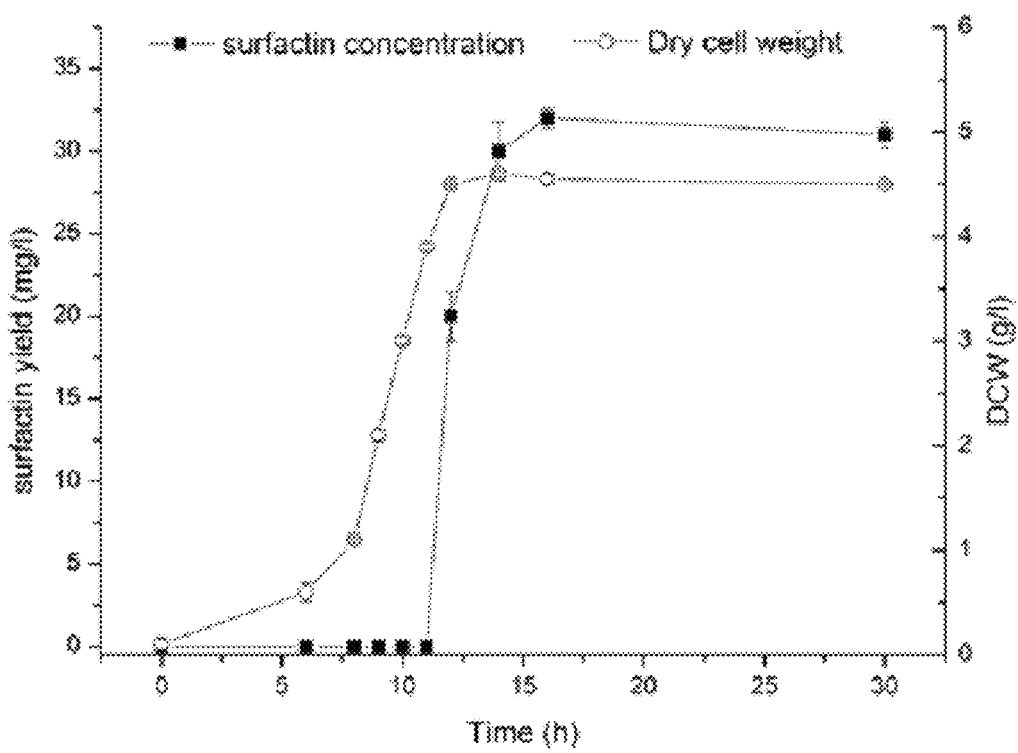
FIG. 3A and 3B are growth curves of *Bacillus amyloliquefaciens* MT45 (FIG. 3B) and a model microorganism *Bacillus subtilis* ATCC 6051 (FIG. 3A) in a fermentation medium and their respective synthetic curve of surfactin.
Figure 3B:
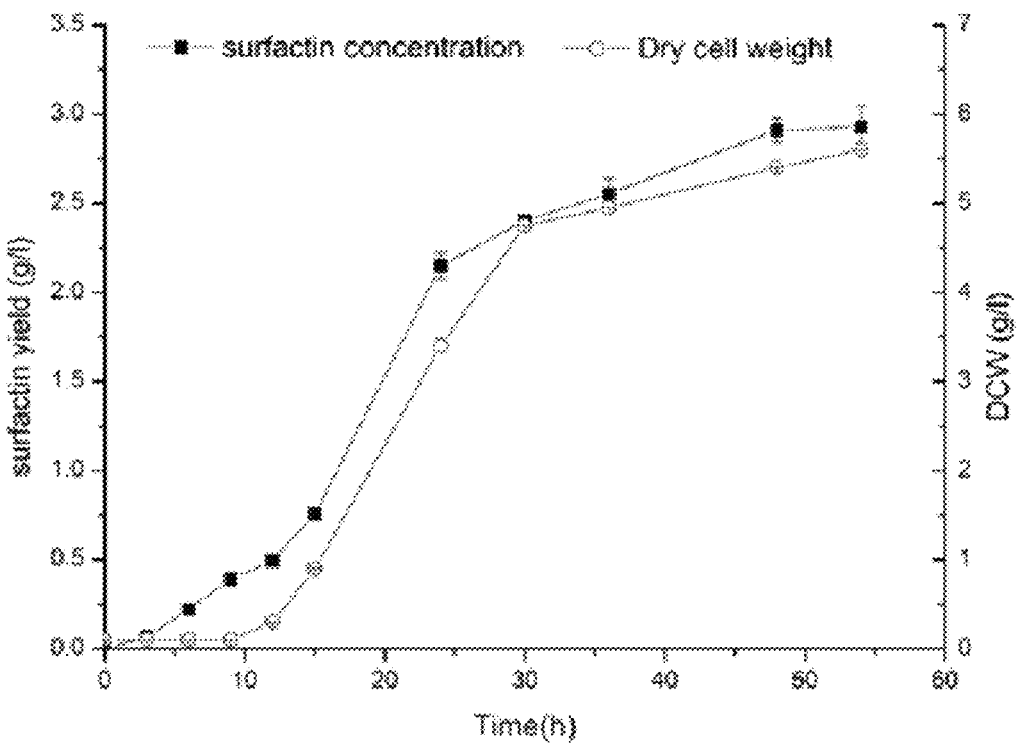

The *Bacillus amyloliquefaciens* MT45 strain identified in Example 3 was activated in the seed medium and then inoculated into a fermentation medium at an inoculum size of 5%. The composition of the fermentation medium was 10 g/L of glucose, 1.5 g/L of peptone, 2 g/L of potassium dihydrogen phosphate, 2 g/L of disodium hydrogen phosphate, and 0.18 g/L of magnesium sulfate. 100 mL of liquid was added into a 500 ml triangular flask and the fermentation was carried out at 37° C., 200 rpm. Samples were taken regularly to determine the amount of cell growth and surfactin production during fermentation. The results were shown in FIG. 3. The *Bacillus amyloliquefaciens* MT45 can synthesize up to 3.0 g/L of surfactin via fermentation time for 55 h.

*Bacillus amyloliquefaciens* MT45 can synthesize surfactin in a super-efficient way, and the highest yield can reach 50% of biomass. The high-concentration surfactin synthesized during culture also reflected the high tolerance of strain MT45 against the product. Compared with a model strain *Bacillus subtilis* ATCC6051, surfactin synthesis was synchronized with the growth of thalli, and the product synthesis had no lag period. These characteristics are beneficial to shortening the fermentation cycle of *Bacillus amyloliquefaciens* MT45, producing more target products, and facilitating the industrial application of MT45 strain.

Example 5 Utilization of Carbon Sources by *Bacillus amyloliquefaciens* MT45

*Bacillus amyloliquefaciens* MT45 can produce surfactin using various saccharides as carbon sources, and the saccharides mainly included sucrose, glucose, fructose, mannose, chitosan, glycerol, soluble starch, and dextrin. Other components of the fermentation medium were: 0.5 g/L of peptone, 2.7 g/L of potassium dihydrogen phosphate, 5 g/L of disodium hydrogen phosphate, and 0.5 g/L of magnesium sulfate. The concentration of the carbon source was 10 g/L. 50 mL of a sample was added into a 250 mL erlenmeyer flask at an inoculum size of 2% and cultured at 37° C., 200 rpm. The results were shown in Table 1.

TABLE 1

Utilization of carbon sources by *Bacillus amyloliquefaciens* MT45

| No. | Carbon source | Surfactin yield in fermentation broth (G/L) |
|---|---|---|
| 1 | Sucrose | 6.65 |
| 2 | Glucose | 3.12 |
| 3 | Fructose | 2.18 |
| 4 | Mannose | 0.20 |
| 5 | Chitosan | 0.17 |
| 6 | Glycerol | 1.74 |
| 7 | Soluble Starch | 0.08 |
| 8 | Dextrin | 0.05 |

Example 6 Utilization of Ammonium Salts by *Bacillus amyloliquefaciens* MT45

*Bacillus amyloliquefaciens* MT45 can produce surfactin using various inorganic ammonium salts, and the inorganic ammonium salts mainly included ammonium nitrate, ammonium sulfate, ammonium chloride, ammonium carbonate, and ammonium bicarbonate. Other components of the fermentation medium were: 20 g/L of sucrose, 0.5 g/L of peptone, 2.7 g/L of potassium dihydrogen phosphate, 5 g/L of disodium hydrogen phosphate, and 0.5 g/L of magnesium sulfate. The concentration of the nitrogen source was 8 g/L. 50 mL of a sample was added into a 250 mL erlenmeyer flask at an inoculum size of 2% and cultured at 37° C., 200 rpm. The results were shown in Table 2.

TABLE 2

Utilization of ammonium salts by *Bacillus amyloliquefaciens* MT45

| No. | Inorganic ammonium salts | Surfactin yield in fermentation broth (g/L) |
|---|---|---|
| 1 | Ammonium nitrate | 8.65 |
| 2 | Ammonium sulfate | 6.81 |
| 3 | Ammonium chloride | 3.42 |
| 4 | Ammonium carbonate | 6.83 |
| 5 | Ammonium bicarbonate | 6.13 |

Example 7 the Production of Surfactin by *Bacillus amyloliquefaciens* MT45 Using Different Fermentation Mediums

*Bacillus amyloliquefaciens* MT45 was inoculated into an LB medium and cultured overnight at 37° C., 200 rpm. A seed solution was transferred to the fermentation medium at an inoculum size of 2%, and cultured at 37° C., 200 rpm for 48 h. The biosurfactant yield of fermentation mediums having different components was shown in Table 3.

TABLE 3

The production of surfactin by *Bacillus amyloliquefaciens* MT45 using different fermentation mediums wherein, LB medium: 10 g/L of peptone, 5 g/L of yeast powder, and 10 g/L of sodium chloride.

| No. | Sucrose g/L | Ammonium nitrate g/L | Peptone g/L | Zinc sulfate g/L | Magnesium sulfate g/L | Potassium dihydrogen phosphate g/L | Disodium hydrogen phosphate g/L | Surfactant yield g/L |
|---|---|---|---|---|---|---|---|---|
| 1  | 30 | 2 | 1.5 | 0.14 | 0    | 4 | 2 | 4.46 |
| 2  | 10 | 6 | 0.5 | 0.14 | 0.18 | 2 | 2 | 0.02 |
| 3  | 10 | 2 | 0.5 | 0.14 | 0    | 2 | 6 | 7.40 |
| 4  | 30 | 6 | 0.5 | 0.14 | 0    | 4 | 2 | 3.38 |
| 5  | 30 | 6 | 1.5 | 0    | 0    | 4 | 6 | 6.11 |
| 6  | 10 | 2 | 1.5 | 0    | 0.18 | 4 | 6 | 7.31 |
| 7  | 10 | 2 | 0.5 | 0    | 0    | 2 | 2 | 0.08 |
| 8  | 30 | 2 | 0.5 | 0.14 | 1    | 2 | 6 | 7.56 |
| 9  | 10 | 6 | 1.5 | 0.14 | 0.18 | 4 | 2 | 8.10 |
| 10 | 30 | 6 | 0.5 | 0    | 0.18 | 4 | 6 | 9.43 |
| 11 | 30 | 2 | 1.5 | 0    | 0.18 | 2 | 2 | 6.63 |
| 12 | 10 | 6 | 1.5 | 0    | 0    | 2 | 6 | 8.50 |

Surfactin extraction: The fermentation broth was centrifuged at 8000 rpm, 4° C. for 10 min. The fermentation supernatant was adjusted to pH 2.0 with 6 mol/L of hydrochloric acid, allowed to stand in a refrigerator at 4° C. for 2 h, and then centrifuged at 12,000 rpm, 4° C. for 30 min to obtain a precipitate. The precipitate was extracted with methanol to obtain crude surfactin.

Example 8 the Preparation of Pure Surfactin Produced by *Bacillus amyloliquefaciens* MT45

Figure 4:
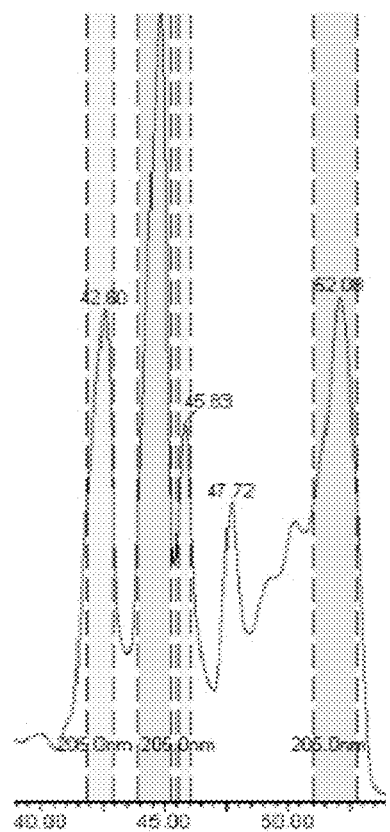
FIG. 4 Purification of surfactin produced by *Bacillus amyloliquefaciens*.

The crude surfactin obtained in Example 7 was purified by Preparative HPLC. A C18 chromatographic column was used, the mobile phases were 0.1% aqueous formic acid and methanol, and the elution conditions were linear elution (30%-70% methanol for 60 min). The detection wavelength of a UV detector was set to 210 nm. The eluted fraction was collected between 40.5 min and 53.5 min, which was subjected to rotary evaporation by a rotary evaporator to remove a solvent to obtain pure surfactin (FIG. 4).

What is claimed is:

1. A method for producing surfactin by using *Bacillus amyloliquefaciens* CGMCC NO.12593, comprising the following steps:
    (a) picking a pure colony of *Bacillus amyloliquefaciens* CGMCC NO. 12593, and activating to obtain a seed culture solution;
    (b) inoculating the seed culture solution obtained in step (a) into a fermentation medium at an inoculum size of 1% to 5%, and culturing at 25 to 37 °C. for 30 to 55 h,
    wherein a formula of the fermentation medium is 10-100 g/L of a carbon source, 1-10 g/L of a nitrogen source, 0.1-1.5 g/L of peptone, 2-10 g/L of potassium dihydrogen phosphate, 2-10 g/L of disodium hydrogen phosphate, and 0-0.2 g/L of magnesium sulfate;
    wherein the carbon source is sucrose, glucose, fructose, mannose, chitosan, glycerol, soluble starch, dextrin, or a combination thereof; and
    wherein the nitrogen source is ammonium nitrate, ammonium sulfate, ammonium chloride, ammonium carbonate, ammonium bicarbonate, or a combination thereof.

2. The method of claim 1, wherein the formula of the seed medium is 2% glucose, 1% yeast powder, and 0.5% sodium chloride, with a natural pH.

3. The method of claim 2, wherein the nitrogen source of the fermentation medium is ammonium nitrate, ammonium carbonate or ammonium sulfate.

4. The method of claim 1, wherein the carbon source of the fermentation medium is glucose or sucrose.

5. The method of claim 1, wherein the nitrogen source of the fermentation medium is ammonium nitrate, ammonium carbonate or ammonium sulfate.

6. The method of claim 1, wherein the formula of the fermentation medium is 10-30 g/L of carbon source, 2-6 g/L of nitrogen source, 0.1-1.5 g/L of peptone, 2-10 g/L of potassium dihydrogen phosphate, 2-10 g/L of disodium hydrogen phosphate, and 0.01-0.2 g/L of magnesium sulfate.

* * * * *

SEQUENCE LISTING

<160> NUMBER OF SEQ ID NOS: 1

<210> SEQ ID NO 1
<211> LENGTH: 1555
<212> TYPE: DNA
<213> ORGANISM: Bacillus Amyloliquefaciens

<400> SEQUENCE: 1

```
tttatcggag agtttgatcc tggctcagga cgaacgctgg cggcgtgcct aatacatgca      60
agtcgagcgg acagatggga gcttgctccc tgatgttagc ggcggacggg tgagtaacac     120
gtgggtaacc tgcctgtaag actgggataa ctccgggaaa ccggggctaa taccggatgc     180
ttgtttgaac cgcatggttc agacataaaa ggtggcttcg gctaccactt acagatggac     240
ccgcggcgca ttagctagtt ggtgaggtaa cggctcacca aggcgacgat gcgtagccga     300
cctgagaggg tgatcggcca cactgggact gagacacggc ccagactcct acgggaggca     360
gcagtaggga atcttccgca atggacgaaa gtctgacgga gcaacgccgc gtgagtgatg     420
aaggttttcg gatcgtaaag ctctgttgtt agggaagaac aagtgccgtt caaatagggc     480
ggcaccttga cggtacctaa ccagaaagcc acggctaact acgtgccagc agccgcggta     540
```

```
atacgtaggt ggcaagcgtt gtccggaatt attgggcgta aagggctcgc aggcggtttc      600
ttaagtctga tgtgaaagcc cccggctcaa ccggggaggg tcattggaaa ctggggaact      660
tgagtgcaga agaggagagt ggaattccac gtgtagcggt gaaatgcgta gagatgtgga      720
ggaacaccag tggcgaaggc gactctctgg tctgtaactg acgctgagga gcgaaagcgt      780
ggggagcgaa caggattaga taccctggta gtccacgccg taaacgatga gtgctaagtg      840
ttagggggtt tccgcccctt agtgctgcag ctaacgcatt aagcactccg cctggggagt      900
acggtcgcaa gactgaaact caaaggaatt gacggggggcc cgcacaagcg gtggagcatg      960
tggtttaatt cgaagcaacg cgaagaacct taccaggtct tgacatcctc tgacaatcct     1020
agagatagga cgtcccctttc gggggcagag tgacaggtgg tgcatggttg tcgtcagctc     1080
gtgtcgtgag atgttgggtt aagtcccgca acgagcgcaa cccttgatct tagttgccag     1140
cattcagttg ggcactctaa ggtgactgcc ggtgacaaac cggaggaagg tggggatgac     1200
gtcaaatcat catgcccctt atgacctggg ctacacacgt gctacaatgg cagaacaaa      1260 gggcagcgaa accgcgaggt taagccaatc ccacaaatct gttctcagtt cggatcgcag     1320
tctgcaactc gactgcgtga agctggaatc gctagtaatc gcggatcagc atgccgcggt     1380
gaatacgttc ccgggccttg tacacaccgc ccgtcacacc acgagagttt gtaacacccg     1440
aagtcggtga ggtaaccttt ttggagccag ccgccgaagg tgggacagat gattggggtg     1500
aagtcgtaac aaggtagccg tatcggaagg tgcggctgga tcacctcctt tctaa          1555
```